(12) United States Patent
Sweeney

(10) Patent No.: US 6,506,165 B1
(45) Date of Patent: Jan. 14, 2003

(54) SAMPLE COLLECTION DEVICE

(75) Inventor: Eamon Charles Sweeney, Dublin (IE)

(73) Assignee: The Provost, Fellows and Scholars of the College of the Holy and Undivided Trinity of Queen Elizabeth near Dublin, Dublin (IE)

(*) Notice: Subject to any disclaimer, the term of this patent is extended or adjusted under 35 U.S.C. 154(b) by 0 days.

(21) Appl. No.: 09/668,468

(22) Filed: Sep. 25, 2000

Related U.S. Application Data

(63) Continuation-in-part of application No. PCT/IE99/00017, filed on Mar. 25, 1999.

(30) Foreign Application Priority Data

Mar. 25, 1998 (IE) .............................. S980225

(51) Int. Cl.[7] .............................. A61B 5/00
(52) U.S. Cl. .............................. 600/562
(58) Field of Search .............................. 600/562–572; 601/93.01–99.04; 251/4, 5, 6, 7, 8, 9, 10

(56) References Cited

U.S. PATENT DOCUMENTS 4,972,843 A * 11/1990 Broden .............. 600/573
5,692,729 A * 12/1997 Harhen .............. 251/4

* cited by examiner

Primary Examiner—Max Hindenburg
Assistant Examiner—Pamela L Wingood
(74) Attorney, Agent, or Firm—Jacobson Holman PLLC

(57) ABSTRACT

A device (1) for acquiring cell samples by aspiration into an evacuated container (3) comprising:

a front hollow needle portion (7) to be inserted into the body from which a sample is to be taken;

a rear hollow needle portion (5) for communication with the evacuated container;

a conduit (11) connecting the front needle portion (7) to the rear needle portion (5);

and a normally closed pinch valve mechanism (6) to open and close the conduit;

The valve mechanism (6) is manually operable by one hand and controls the application of negative pressure in the front needle portion (7). The conduit may comprise a flexible tube and the valve mechanism (6) may comprise releasable means (8) to pinch the flexible tube in a pressure-tight manner. The valve mechanism (6) may comprise a spring-biased push-button (8) operable by one digit of a user's hand.

11 Claims, 6 Drawing Sheets

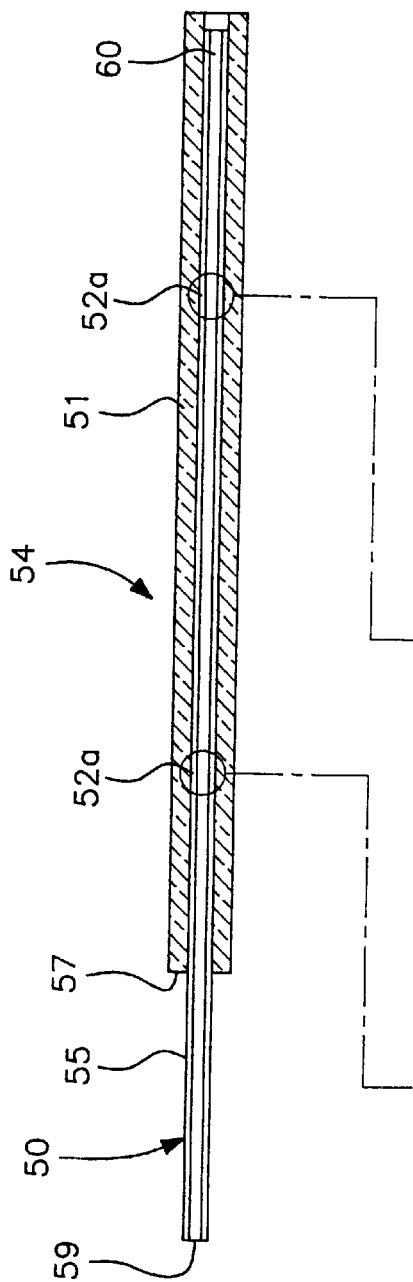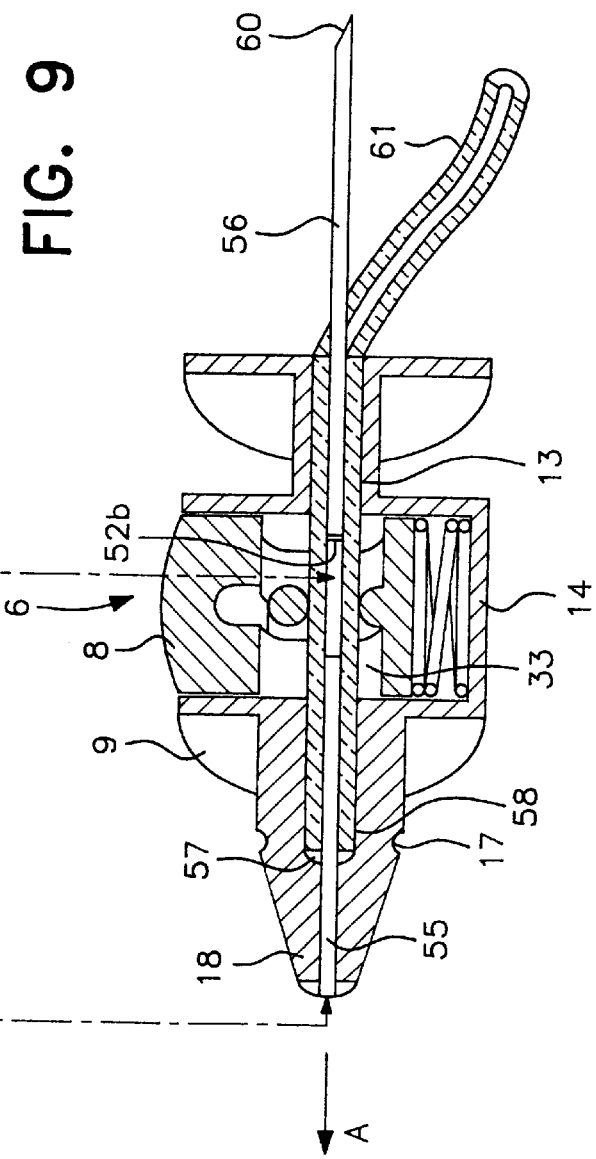

SAMPLE COLLECTION DEVICE

This is a Continuation-in-Part of PCT International Application No. PCT/IE99/00017, filed Mar. 25, 1999.

This invention relates to devices for acquiring cell samples, particularly for medical or laboratory analysis. It is primarily directed to a biopsy device for obtaining tissue and cell samples for analysis but devices according to the invention are also useful for obtaining fluid samples, in particular blood. The device may be used in either human or veterinary medicine or in post-mortem examination.

In the diagnosis of human disease it is often necessary for the clinician, physician, or surgeon to obtain a sample of tissue or cells from the patient for examination by medically qualified tissue or cell analysts (histo or cytopathologists). Such samples may be obtained by open surgical biopsy, or by endoscopic biopsy, using specially designed forceps. Both these procedures are traumatic and expensive. Alternatively cell samples of the relevant tissue may be obtained by inserting a hollow needle (e.g. a standard blood sampling needle) into a lesion, and moving the cutting point backwards and forwards several times. The cells thus dislodged are taken up into the needle either by force of capillary attraction, or by the additional use of suction provided by a syringe, e.g. a standard 10 or 20 ml syringe. Using the needle alone, the sample obtained may be very small, or even inadequate. Tissue or cell material may be lost or wasted. Using the syringe increases the yield in most instances, but it is a difficult manoeuvre for untrained clinicians, or clinicians who do not perform the procedure on a regular basis. To overcome this latter difficulty, a pistol-type syringe holder known as a Swedish gun was developed which would allow the application of suction, and simultaneous passage of the needle, through the tissue using one hand only. For most people this instrument proves extremely awkward, inaccurate and traumatic. In addition the use of this physically large and intimidating device causes severe distress to patients in many instances.

It is well known in the field of phlebotomy (blood-sampling) to use an evacuated container for receiving blood samples. A hollow needle having front and rear pointed ends is mounted in a plastic needle holder. The front end of the needle is inserted into a vein and the rear end of the needle pierces a stopper or diaphragm on an evacuated tube which is slidable inside the needle holder. Blood is then sucked through the needle into the container. It is not generally necessary to interrupt the flow of blood until the required sample has been taken or the container is full. The container is then removed (while the front end of the needle may be retained in the vein) and a second evacuated container may be brought into use.

U.S. Pat. No. 4,697,600 suggests the use of an evacuated container in needle aspiration biopsy. It describes a method for obtaining tissue and cells by inserting one end of a fine hollow needle into an area of body tissue and inserting the other end into an evacuated container with pre-established vacuum. This is followed by continuously suctioning tissue and cell samples through the needle into the container. However with this device, after the rear end of the needle has pierced the stopper or diaphragm on the evacuated container, it is not possible to control the application of the vacuum precisely to the area to be sampled. The needle must be inserted into the body tissue before the evacuated container can be pushed into the holder, which involves a potentially distressing movement. Furthermore, once the hollow needle is removed from the body tissue the vacuum is lost. It is therefore necessary to use a second evacuated container, post removal from the tissue sample, to ensure that all tissue and cell samples are collected from the needle and into the container. Furthermore it is not possible to use the vacuum to suck preserving solution into the container after aspiration of the samples.

Known phlebotomy devices, and also the device of U.S. Pat. No. 4,697,600 suffer from the problem that the front end of the needle must be inserted into the vein or body tissue before the evacuated tube is pushed forward inside the needle holder. If the rear end of the needle pierces the stopper or diaphragm of the evacuated tube prematurely, the vacuum will be lost. It is however difficult to push the evacuated tube forward without a risk of traumatizing the vein or tissue in which the front end of the needle has been inserted.

Various proposals have been made for valve mechanisms in phlebotomy equipment e.g. WO 95/16395 and WO 95/28881. However these valves are intended to close the cannula to fluid flow except when an evacuated tube is in place and connected to the rear end of the cannula. U.S. Pat. No. 3,848,579 describes a blood-drawing device which has separate front and rear cannulas with an elasto-valvular mechanism between them. Various forms of valve are described, all of which are automatically activatable by application of the vacuum to the rear cannula. The valve mechanism prevents the occurrence of blood drips from the venous side into the ambient environment prior to the installation of the initial evacuated tube and/or during the span of time required to change from one blood-filled tube to a fresh evacuated tube, as occurs during the process of multi-sampling involving a single venipuncture. However the valve mechanism cannot be operated while the vacuum is applied to the cannula conduit.

U.S. Pat. No. 3,906,930 describes a blood-taking device having two valves. The first valve closes the rear end of the needle when a container is not connected to it and the second valve makes it possible to control the difference of pressure utilized for drawing blood. The second valve can be closed rapidly in the event it is discovered that the needle lies in tissue exterior to a blood vessel rather than in a blood vessel itself. The device is a relatively complex structure made in two joinable portions. The first valve is operated by joining and separating the two portions. The second valve is operated by rotating the container relative to the device. The problem with this device is that it would require 2 hands for operation and would be clumsy to use, with a risk of distress to the patient.

EP 033 528 describes a blood sampling device having a flexible tube linking two opposing needles. A variety of different valve means are provided, including using the user's fingers to pinch the tube, the application of a roller valve and the provision of a cap. In all the described embodiments the flexible tube is in a normally open state and the valve is actuated to seal the tube. Such an arrangement is unsuitable for multiple passing tissue sampling.

WO 88/10286 describes disadvantages associated with blood sampling devices having normally closed valves, specifically the issue of sterilization of the valve and possible failure of the device due to wear and tear resulting from continual strain on the valve. WO 88/05286 addresses these problems by providing a cover for the device, the cover adapted to maintain the normally closed valve in an open position.

It is an object of the present invention to provide devices which can be used by clinicians to obtain cell samples with minimal distress to the patient or animal and in particular, in the case of a biopsy device to improve the chances of successfully recovering adequate tissue or cellular material for a testing while subjecting the cells and tissues to minimal shear and other stresses.

Accordingly the present invention provides a device and method for obtaining tissue or cellular samples as described in the appended claims.

The present invention provides a device for acquiring tissue or cell samples by aspiration into an evacuated container, the device comprising:
- (a) a front hollow needle portion to be inserted into the body from which a sample is to be taken,
- (b) a rear hollow needle portion for communicating with the evacuated container,
- (c) a conduit connecting the front needle portion to the rear needle portion,
- (d) a valve mechanism to open and close the conduit, characterized in that the valve mechanism is manually operable by one hand and controls the application of negative pressure in the front needle portion.

In a preferred embodiment, the conduit comprises a flexible tube and the valve mechanism comprises releasable means to pinch the flexible tube in a pressure-tight manner. The flexible tube may suitably be of silicone or other elastomeric plastics material which is acceptable in the medical/veterinary field. The term "pressure tight" and/or "air-tight" as used herein refers to a degree of tightness which is sufficient to inhibit a significant passage of air under the negative pressure applied by the type of evacuated container which is to be used.

More preferably, the valve mechanism comprises a spring-biased push-button operable by one digit of a user's hand.

Suitably, the front and rear needle portions and the conduit are mounted longitudinally in a housing, and the valve mechanism comprises a slide member which is moveable transversely of the housing between a rest position and an activated position. Preferably the front and rear needle portions and the conduit are in alignment.

Preferably, the conduit comprising a flexible tube passes through an aperture in the slide member and is pinched against a fixed element of the valve mechanism when the slide member is in the rest position and is released to open the conduit when the slide member is in the activated position.

In the preferred embodiment the housing is manufactured from a translucent or transparent material.

In one embodiment which allows for ease of assembly of the device, one part of the conduit and the rear needle portion are formed from an elongate rigid tube provided with a break point at which the tube is breakable into front and rear parts, and a second part of the conduit is formed by flexible sheathing on the rigid tube.

In one embodiment the device may be used in the practice of tissue sampling. In another embodiment the device may be used in the practice of phlebotomy.

In further embodiments the device may be used in the practice of veterinary sampling, or for acquisition of samples in post-mortem examination.

The invention also relates to a method of acquiring body samples by aspiration into an evacuated container, utilizing a device comprising:
- (a) a front hollow needle portion to be inserted into the body from which a sample is to be taken,
- (b) a rear hollow needle portion for communicating with the evacuated container,
- (c) a conduit connecting the front needle portion to the rear needle portion,
- (d) a valve mechanism to open and close the conduit the valve mechanism being manually operable by one hand and controlling the application of negative pressure in the front needle portion, the method comprising the steps of:
  - (i) establishing communication between a pre-evacuated container and the rear hollow needle portion;
  - (ii) inserting the front needle portion into the body from which the sample is to be taken at the appropriate location for obtaining the desired sample;
  - (iii) actuating the valve mechanism for sufficient time, and repeatedly if desired, to apply negative pressure in the front needle portion so as to draw a sample through the front needle portion through the conduit to the rear needle portion and into the pre-evacuated container.

One embodiment of the invention will now be described by way of example, with reference to the accompanying drawings.

BRIEF DESCRIPTION OF DRAWINGS

FIG. 8 shows a sectional view of a steel tube sheathed with a flexible tubing.

FIG. 9 shows a cross sectional view of an assembled valve mechanism.

DETAILED DESCRIPTION OF THE DRAWINGS

Figure 1:
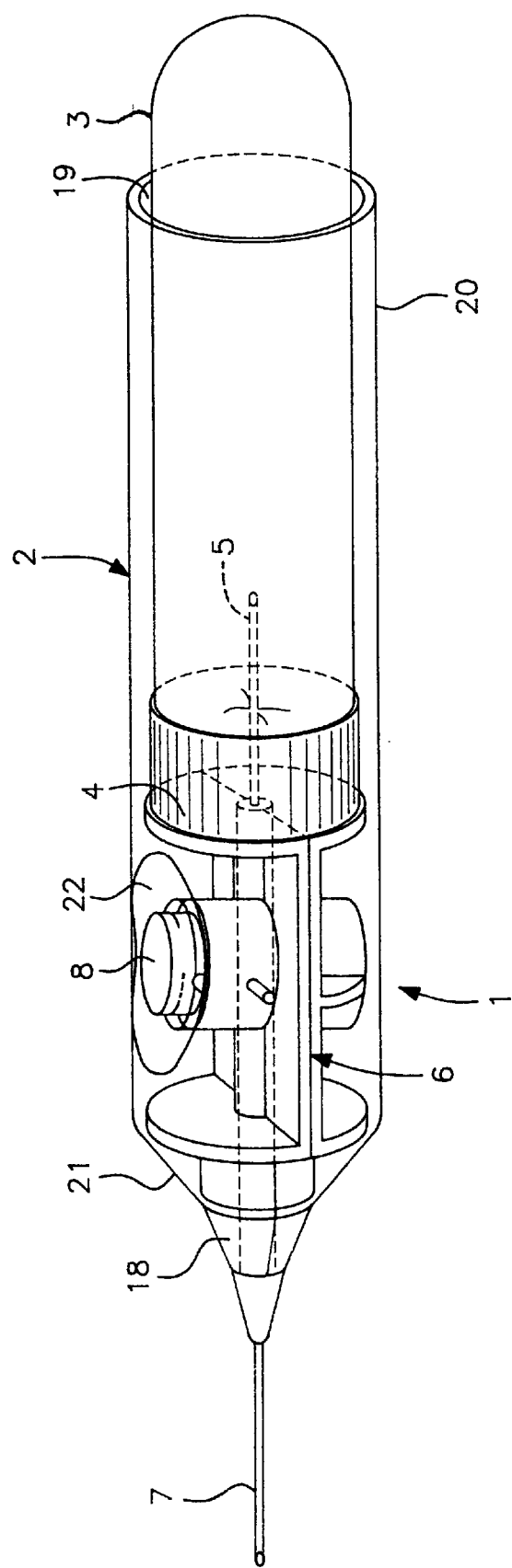
FIG. 1 shows a pictorial view of a device in accordance with one embodiment of the invention.

FIG. 1 shows a hand-held sample acquiring device 1, according to one embodiment of the invention. Due to the use of transparent materials, interior components of the device are visible. The device consists of a generally cylindrical hollow holder 2 which is open to the rear in order to receive a pre-evacuated tube 3 of the type conventionally used in phlebotomy, for example as sold under the Trade Mark VACUTAINER. The tube 3 is closed by a pierceable cap 4 and is slidable within the cylindrical skirt 20 of the holder.

A normally closed pinch valve mechanism 6 is located predominantly within the front region of the holder 2. The holder has a frusto-conical front end 21 through which the front tip 18 of the valve mechanism projects. The tip 18 is designed to receive a front hollow needle or cannula 7 in an air-tight manner which permits the needle to be mounted and removed easily. In the preferred embodiment shown in the drawing, the needle mounting on the tip is of the kind which is commercially available under the trade mark LUER.

A rear hollow needle or cannula 5 projects rearwardly from the valve mechanism 6 and extends axially within the cylindrical skirt 20 of the holder. When the tube 3 is present inside the holder 2, the needle 5 pierces the cap 4 so that the needle communicates with the evacuated interior of the tube 3.

Figure 2:
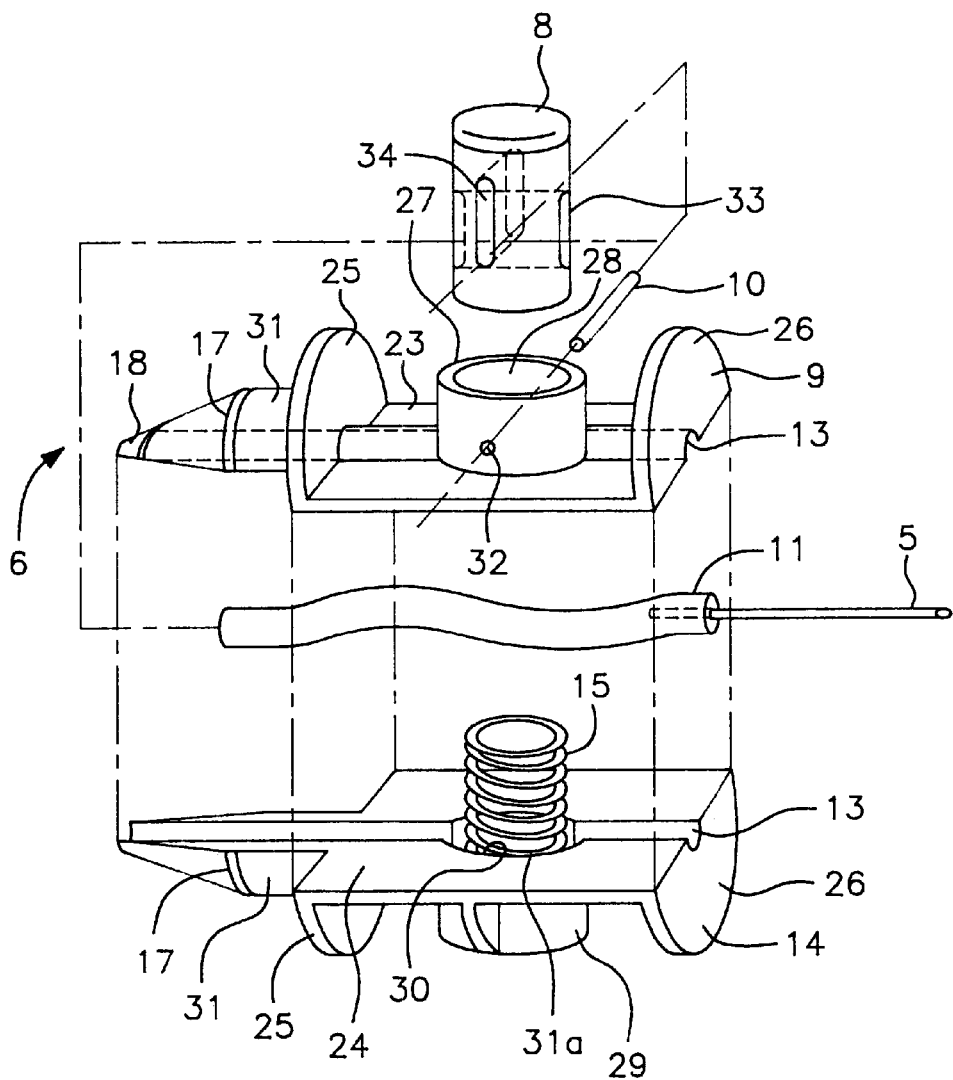
FIG. 2 shows an exploded view of the components of a valve mechanism for the device of FIG. 1.

The front and rear hollow needles are connected by a conduit which passes through a passage in the valve mechanism 6. The conduit is not shown in FIG. 1 but is shown in FIG. 2 and identified by reference numeral 11. The mechanism is operated by a push button 8 which extends through a dished aperture 22 in the cylindrical wall of the holder 2. It can be moved by pressure of a single digit of a user's hand and slides transversely of the holder (i.e. up and down as shown in the drawings).

The components of the pinch-type valve mechanism are shown in greater detail in FIG. 2. The mechanism is based on a pair 9, 14 of body portions, suitably of moulded plastics material. Each of the body portions comprises a flat plate 23, 24 with a pair of semi-circular flanges 25, 26 extending therefrom so that when the body portions are assembled together (as in FIG. 3) a pair of circular discs are formed. These discs are of marginally smaller diameter than the internal diameter of the skirt 20 of the holder 2 so that the discs are slidable inside the skirt and serve to position the valve mechanism concentrically within the holder.

The top body portion 9 has a hollow boss 27 with an open mouth extending radially from the plate 23 and defining a cylindrical slideway 28 which is aligned with an aperture in the plate 23 and which is open at the top. The bottom body portion 14 has a corresponding hollow boss 29 having base and defining a slideway 30 aligned with an opening 31a in the plate 24. A spring 15 is received in the lower slideway 30 and contacts the base of the boss 29. A cylindrical slide member in the form of push button 8 is received in both the top and bottom slideways. It will be appreciated that the slideways and push button in other embodiments could have a rectangular or other cross-sectional shape.

Each body portion extends forwardly of flange 25 in a nose portion 31 which is initially semi-cylindrical and then semi-conical. At the junction between the semi-cylindrical and semi-conical portions there is an annular groove and a lip 17 which stands proud of the surface.

The plates 23, 24 and nose portions 31 are each formed with a channel 13 so that when the body portions are assembled together a longitudinal cylindrical passage is formed through the assembly. A deformable, compressible or flexible tube 11, for example of silicone rubber material, is received in this passage and crosses the aligned slideways 28, 30 at right angles thereto. The rear hollow needle 5 is also received in this passage and its front end is inserted in an air-tight manner in the rear end portion of the tube 11.

The upper boss 27 has a pair of diametrically opposed apertures 32 through which a locking bar 10 can be inserted at right angles to the passage 13. The push button 8 has two vertically orientated apertures or slots 33, 34 extending across it at right angles to one another. The flexible tube 11 can pass in the longitudinal direction through slot 33 and the locking bar 10 can pass at right angles thereto through slot 34.

Figure 3:
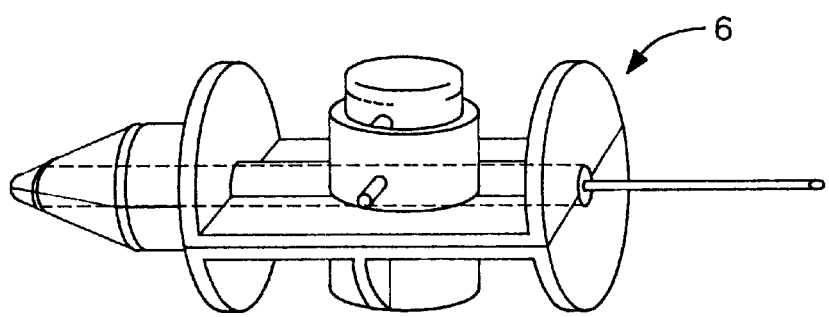
FIG. 3 shows the completed valve mechanism.

In assembling the valve mechanism, the spring 15 is inserted into the slideway 30 in the bottom body portion, the push button 8 is inserted into the slideway 28 in the top body portion and the locking bar is pushed through the apertures 32 and slot 34. The flexible tube 11 is then threaded through the slot 33 in the button, and the tube and front portion of the rear needle 5 are laid in the channel 13. The two body portions are then joined together, e.g. by welding, by adhesive, by a snap fitting (not shown) or other air-tight joining method. The front end of the flexible tube 11 is sealed in the passage 13 by adhesive or the like. The spring is compressed in the slideway 30 and acts against the lower end of the button 8. FIG. 3 shows the completed valve mechanism.

Figure 4:
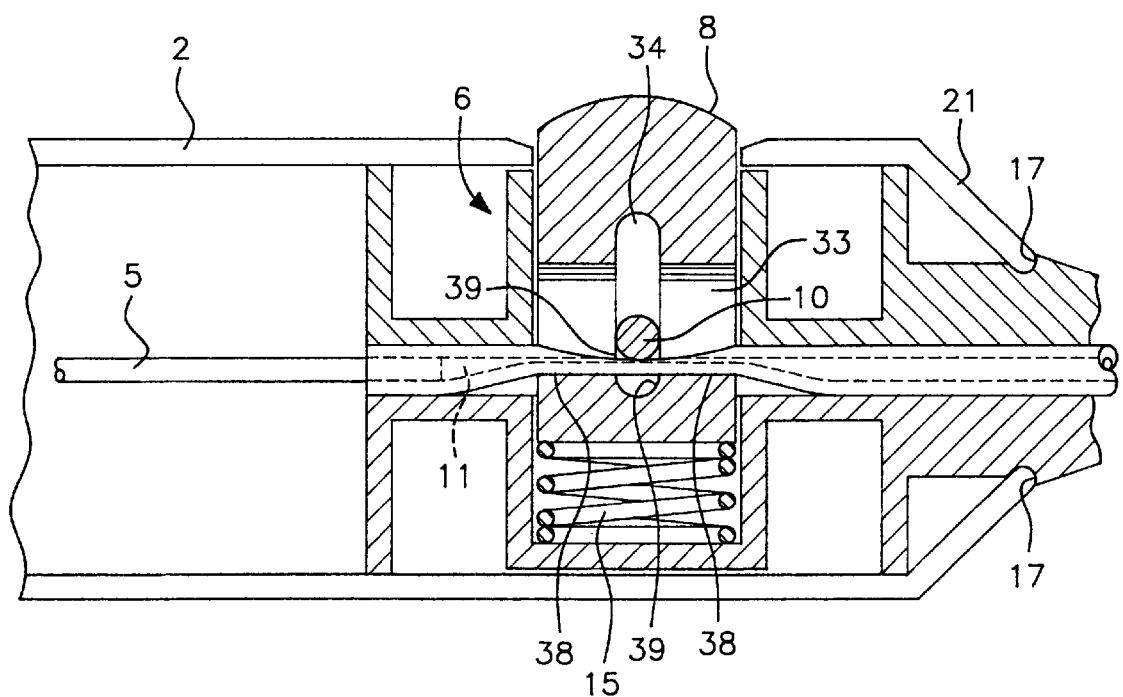
FIG. 4 is a vertical cross-section of part of the holder and the valve mechanism, showing the valve mechanism in the rest (closed) position.
Figure 5:
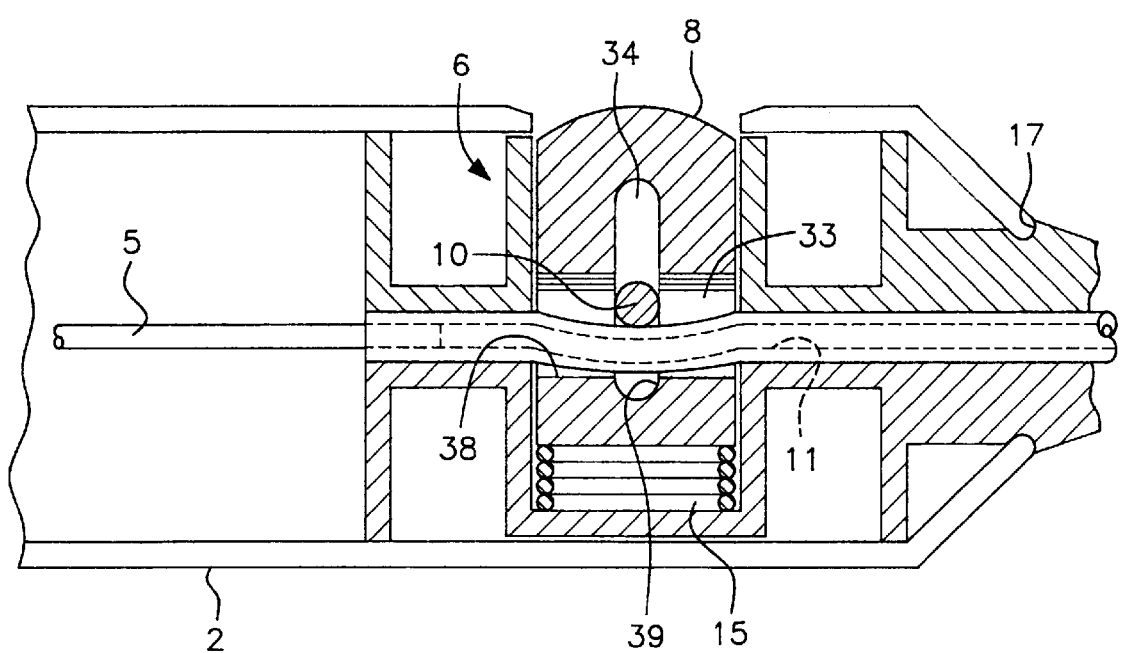
FIG. 5 is a cross-section similar to FIG. 4, showing the valve mechanism in an activated (open) position.

The press button 8 is then pushed downwardly and the completed valve mechanism is inserted into the holder through the open end 19 and pushed until it reaches the position shown in FIGS. 1, 4 and 5. The conical portions and point 18 of the nose portion 31 of the valve mechanism pass through the frusto-conical portion 21 of the holder and the front edge of the frusto-conical portion 21 snaps into the groove behind the lip 17. It will be apparent that other co-operating arrangements can be used for securing the valve mechanism in position. The push button 8 snaps out through the aperture 22, urged by the spring 15 which acts against the opposed bottom part of the wall of the holder.

As shown in FIG. 4, when the valve mechanism is in the rest position, the spring 15 acting on the push button 8 presses the flexible tube 11 (which is passing through slot 33) against the locking bar 10 (which is held in the apertures 32), thus pinching the tube 11 in a pressure-tight manner. This pinching is effected by the abutment of the lower face 38 of slot 33, particularly at the corners 39, against the flexible tube 11 thus pressing the flexible tube 11 against the locking bar 10. The conduit between the rear needle 5 and front needle 7 is formed by the flexible tube 11 and part of the passage 13 extending from the front end of the tube 11 to the front needle 7 on tip 18. This conduit is closed in an air-tight manner by the pinching of the tube. The pinching does not disturb the seal between the rear needle 5 and the rear end of the tube 11, or the seal between the front end of the tube 11 and the front part of the channel 13. Negative pressure applied by the evacuated container 3 to the rear needle 5 is therefore not applied to the front needle 7.

When the push button is depressed by finger pressure against the action of the spring 15, as shown in FIG. 5, the pinch effect on the tube 11 is released, thus opening the conduit between rear needle 5 and front needle 7 so that vacuum is applied at the front tip of the front needle. When the push button is released, the spring 15 acts again to pinch the tube 11. The reduced pressure in the container 3 is maintained until the push button is depressed.

Figure 6:
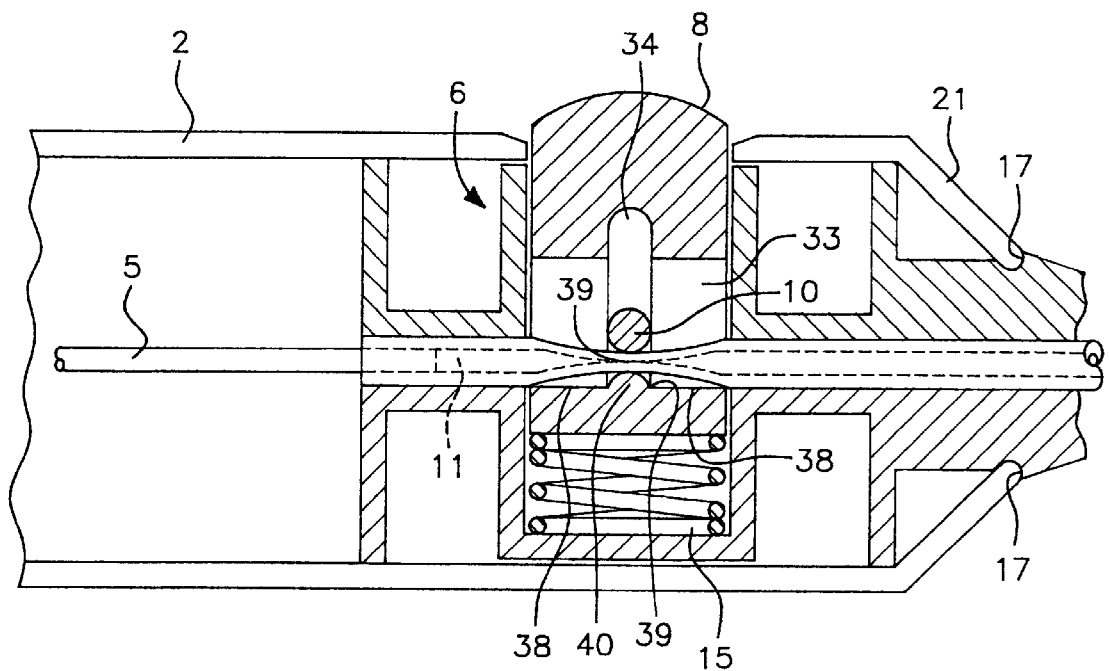
FIG. 6 is a cross-section corresponding to FIG. 4, showing a second embodiment.
Figure 7:
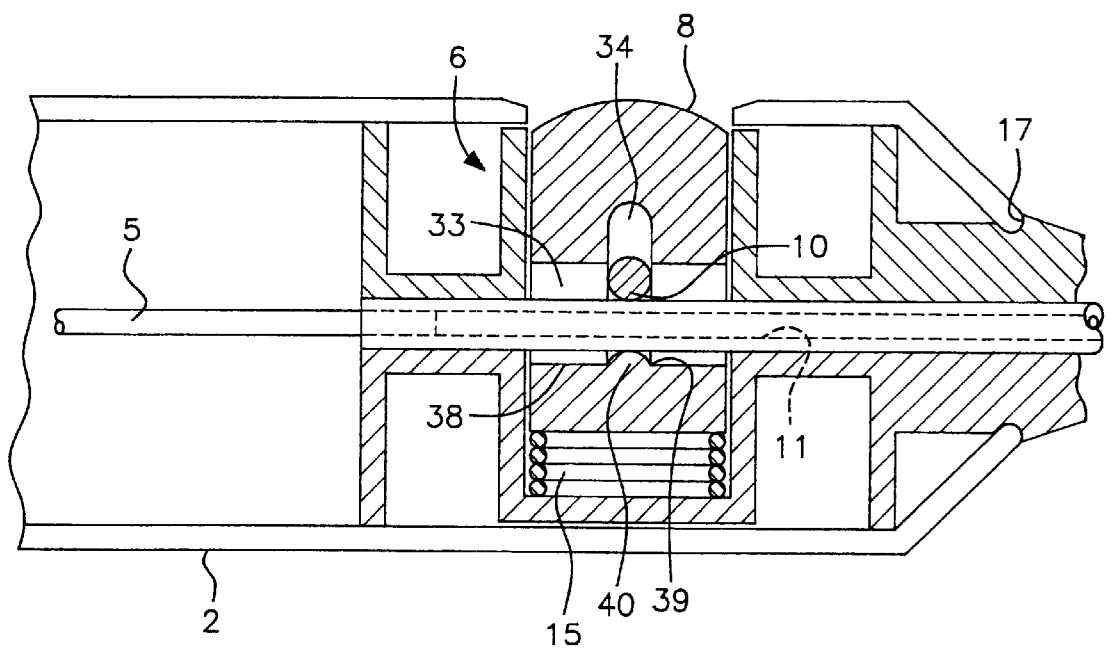
FIG. 7 is a cross-section corresponding to FIG. 5, showing the second embodiment.

FIGS. 6 and 7 show a second embodiment having an alternative mechanism for effecting the pinching of the tube 11 against the locking bar or pin 10. A rib or protrusion 40 is formed on the lower face 38 of slot 33 extending at right angles to the passage 13, i.e. parallel to the locking bar 10. The rib 40 may be integral with the material of the button 8, or alternatively it may be formed by a bar laid in the bottom of slot 34 (see FIG. 4). When the press button is in its rest position i.e. compressing the tube 11, the tube is pinched between the rib 40 and the locking bar 10. The closure of the conduit in an air-tight manner by the pinching of this embodiment results in a more concentrated pinching as compared with that effected in the embodiment of FIG. 4. FIG. 7 is a similar view to that described with reference to FIG. 5 showing the push button in an activated state. As such the rib 40 has moved away from the tube 11, releasing the pinch effect on the tube and thus opening the conduit between the rear needle 5 and the front needle 7 so that a vacuum is applied at the front tip of the front needle 7.

An alternative method of assembling the valve mechanism 6 is shown in FIGS. 8 and 9. FIG. 8 shows an assembly 54 comprising a single length of 22 gauge steel tubing 50 which is partly sheathed by a flexible tubing 51. In the embodiment shown the flexible tubing is silicon tubing. The steel tube 50 is frangible having snap or break points which in the embodiment shown are formed by circumferential grooves 52a, 52b scored (for example by filing) in the outer surface of the steel tube 50. The valve comprises two body portions (9,14) as described above. The assembly 54 is laid in the channel 13 in one of the body portions (and through the slot 33 in the push button 8) as per the assembly operation described above particularly with reference to FIG. 2. The rigidity of the assembly 54 imparted by the steel tube 50 allows ease of insertion of the assembly into the channel 13. Once the assembly 54 is inserted, sufficient force is applied to the steel tube 50 at the break point 52b to snap the steel tube in two—forming a front tube portion 55 and a rear tube portion 56. The body portions are then brought together in a snap-fit or other such arrangement as described above. The assembled arrangement is shown in cross-sectional view in FIG. 9. The front tube portion 55 protrudes from the tip 18 of the device. The front tube portion 55 may then be gripped and pulled axially in the direction of the arrow A separating the front portion 55 from the rear portion 56. The front portion 55 is pulled sufficiently far forward to leave an adequate amount of the silicone tubing 51 free of support from the steel tubing to allow the valve mechanism 6 (as described above) to operate as described previously and so that the circumferential groove 52a is positioned at the front end of the tip 18. This separation action aids the firm seating of the front end 57 of the silicon tubing in a socket or seat 58 recessed in the tip 18. The seat 58 may be arranged concentrically with the annular groove behind the lip 17 described above. Alternatively the channel 13 could be tapered to grip the front end 57 of the tubing firmly. It will be noted that in the device shown in FIG. 9 the silicon tubing 51 stops rearwardly of the tip 18. The joining of the body parts of the device creates a seal directly between the tip 18 and the front portion of the steel tube 55. This may avoid the necessity to provide an additional seal between the tip 18 and the front portion of the steel tubing.

Separating the front and rear parts of the steel tube may result in excess tube extending from the tip 18. Excess steel tube comprising the portion of the tubing between the break point 52a and the front end 59 of the steel tube may be snapped off at break point 52a to leave the steel tube flush with the end of the tip 18 and a part of the front portion 55 forming part of a conduit. The rear portion 56 of the steel tube forms a rear needle portion. The rear end point 60 of the steel tube may be bevelled. The rear needle portion and part of the conduit may thus be formed in-situ. Similarly, the rear portion 56 of the tubing extending from the rear end 60 to the break point 52b forms a rear needle portion. The break point 52b is located an appropriate distance along the steel tubing 50 so that the rear portion 56 does not impede the valve mechanism 6. Excess sheathing 61 of silicon tubing can be stripped away. The entire assembled mechanism can then be inserted in a holder as described above, and a needle may be fitted onto the tip 18.

The holder 2 and if desired the valve mechanism 6 may suitably be manufactured from a translucent polymer. The device 1 is held between the thumb, index and middle fingers of one hand of a user, allowing precise localization of the needle 7 with minimal wobble and easy multipass sampling. The side walls of the holder may have depressions in the front region of the exterior surface to accommodate fingers in a non-slip manner. By maintaining the valve 6 in a closed position it is possible to withdraw the sample removal device completely from a tissue sample without losing the vacuum. As such, one of the major benefits of the system is the ability, after the needle has been withdrawn, to flush the entire sampling channel with biological fluid medium into the evacuated tube 3. This ensures that cellular material is neither lost nor wasted and the sample can be subjected to a much wider variety of analysis than is normally the case. In addition, by removing the needle 7 after sampling and expressing a aliquot of the specimen contained therein onto a slide, the slide can be smeared and stained by a method such as that known as Diff-Quik, thus enabling rapid near-patient assessment of both the adequacy and nature of the material obtained.

The range of conditions which can be investigated more readily with this invention include; cancers (especially those of the breast, thyroid and any visceral cancer which has spread to the superficial lymph nodes), infections (such as tuberculous or fungal infections involving nodes), cysts of various organs and primary malignancies of the lymphoid system (lymphoma).

The device of the invention is of such simple construction that it is suitable for "one-trip" use and can economically be disposed of after a sample has been taken from a single patient. The device is no larger than a standard syringe, is held in one hand and operated and controlled by the finger-tips of that hand. As a result of its manoeuvrability, there is less danger of needle-stick injury to the fingers of the other hand which are used to localize, palpate and fix the tissue lesion during the procedure. As such it is safer for the user than conventional devices or procedures. The device is so valved as to allow control of the application of vacuum precisely to the area to be sampled. Additional features which improve the utility of the device include the use of a translucent or transparent polymer composition for the holder and the valve mechanism which allows visualization of the sample pathway and that permits intraprocedural assessment of the adequacy of the sample.

Mode of Operation

The area to be sampled is prepared according to standard practice. The sample removal device 1 is removed from its packaging and a pre-evacuated tube 3 is inserted into the open end such that the needle 5 penetrates the flanged rubber stopper 4, and is visible within the tube. The needle and pre-evacuated tube are then in communication with each other. Once the pre-evacuated tube has been firmly seated it is important that the push-button 8 of the valve 6 is not depressed until the tip of the sampling needle 7 has been inserted into the tissue. Failure to observe this will result in a loss of vacuum.

The sampling needle 7 is attached to the device, ensuring that the needle hub is firmly seated and air-tight. A 22 gauge needle is most commonly used but the hub can be adapted to existing hub fittings of medical needles of a variety of gauges, according to the circumstances.

Figure 10:
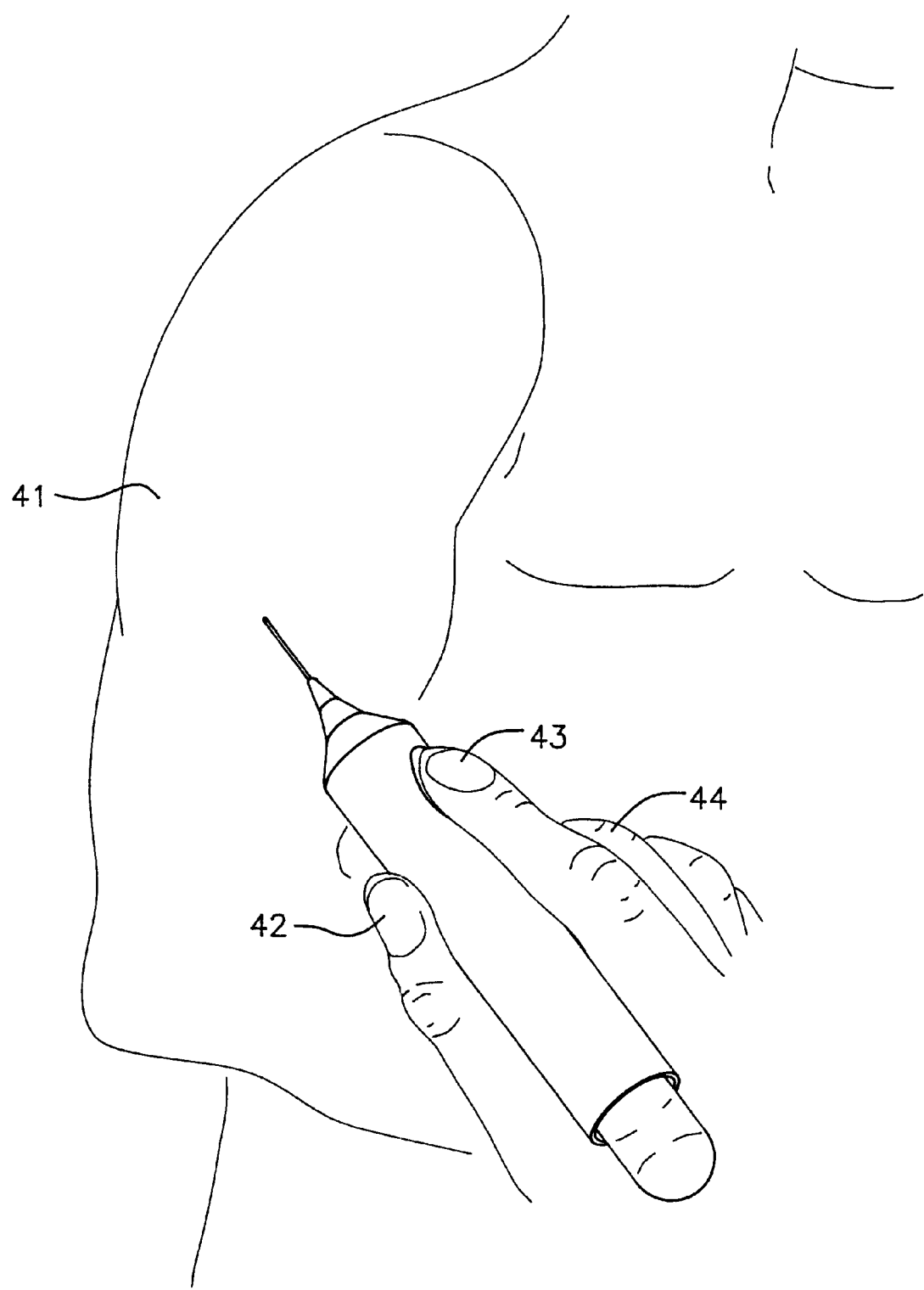
FIG. 10 shows the device of FIG. 1 being utilized to extract a sample from a body.

As shown in FIG. 10 the sampling needle is inserted into the body 41 (for example through a lesion) in the normal manner. During insertion the instrument may be held between the thumb 42 and index finger 43. When the needle 7 is satisfactorily situated (as shown in FIG. 10) the hold on the instrument is shifted to the thumb 42 and middle finger 44, allowing the index finger 43 to depress the button 8.

After an adequate number of passes and before the needle is withdrawn from the skin, the button is released. If blood becomes visible in the needle hub or internal tubing of the instrument during the procedure, the button should be released immediately or haematoma formation may occur and/or the specimen may be excessively haemodilute.

At this stage the sampling needle may be removed and a smear made of its contents for rapid assessment of specimen nature and adequacy. At no time during this interval should the button be depressed.

If the sampling needle has been removed for the above purpose it should now be reattached and dipped in an adequate amount of freshly prepared Hank's solution. The button is depressed and as much fluid as the vacuum permits is drawn into the specimen and should be sent to the laboratory for immediate analysis.

A second use of the sample removal device involves the device 1 being used in the practice of phlebotomy. The mode of operation is the same as that outlined above, with the exception that the sampling needle is inserted into a blood vessel, not into tissue, and numerous passes are not required. The valve may be closed when a fresh evacuated container is being substituted for a container into which blood has been aspirated.

In order to facilitate an appropriate angle of entry into the skin for blood letting purposes, the front needle may be mounted on an eccentric hub offset from the axis of the valve mechanism but connected thereto by the conduit.

The terms "top, bottom, up, down" and the like are used herein with reference to the operation of the device shown in the drawings and do not necessarily describe the position when the device is in use.

The words "comprises/comprising" and the words "having/including" when used herein with reference to the present invention are used to specify the presence of stated features, integers, steps or components but does not preclude the presence or addition of one or more other features, integers, steps, components or groups thereof.

What is claimed is:

1. A device (1) for acquiring tissue or cell samples by aspiration into an evacuated container (3), the device comprising:
   (a) a front hollow needle portion (7) to be inserted into a body from which a sample is to be taken,
   (b) a rear hollow needle portion (5) for communicating with the evacuated container (3); and
   (c) a conduit (11) connecting the front needle portion (7) to the rear needle portion (5),
   characterized in that the conduit (11) comprises a flexible tube, and a pinch valve mechanism (6) is provided to open and close the conduit and to control the application of negative pressure in the front needle portion, the valve mechanism (6) being manually operable by one hand and comprising a slide member (8) moveable between a rest position in which it pinches the flexible tube in a pressure-tight manner against a fixed element (10) of the valve mechanism (6), and an activated position in which it opens the conduit.

2. A device (1) according to claim 1 wherein the valve mechanism (6) comprises a spring-biased push-button (8) operable by one digit of a user's hand.

3. A device (1) according to claim 1 wherein the front (7) and rear (5) needle portions and the conduit (11) are mounted longitudinally in a housing, and the valve mechanism (6) comprises a slide member (8) which is moveable transversely of the housing between a rest position and an activated position.

4. A device (1) according to claim 3 wherein the front (7) and rear (5) needle portions and the conduit (11) are in alignment.

5. A device (1) according to claim 3 wherein the conduit (11) comprises a flexible tube which passes through an aperture (33) in the slide member (8).

6. A device (1) according to claim 5 wherein the flexible tube is pinched between a fixed element (10) of the valve mechanism and a part (40) of the slide member.

7. A device (1) according to claim 1 having a spring (15) acting to pinch the tube in a pressure-tight manner when the valve mechanism (6) is in the rest position.

8. A device (1) according to claim 3 wherein the housing is manufactured from a translucent or transparent material.

9. A device (1) according to claim 1 wherein one part of the conduit and the rear needle portion (5) are formed from an elongate rigid tube (50) provided with a break point (52*b*) at which the tube is breakable into front (55) and rear (56) parts, and a second part of the conduit (11) is a flexible tube formed by flexible sheathing which was on the rigid tube and which is free of support by the rigid tube (50) between the front (55) and rear (56) parts thereof.

10. A device (1) for acquiring tissue or cell samples by aspiration into an evacuated container (3), the device (1) comprising:
    (a) a front hollow needle portion (7) to be inserted into a body from which a sample is to be taken,
    a rear hollow needle portion (5) for communicating with the evacuated container (3); and
    a conduit (11) connecting the front needle portion (7) to the rear needle portion (5),
    characterized in that the conduit (11) comprises a flexible tube, and a pinch valve mechanism (6) is provided to open and close the conduit (11), the valve mechanism (6) comprising a push-button releasable means (8) to pinch the flexible tube (11) in a pressure-tight manner against a fixed element (10) of the valve mechanism when in a rest position and to release the pinch effect when the push-button is depressed.

11. A method of acquiring tissue and cell samples by aspiration into an evacuated container (3), utilizing a device (1) comprising:
    (a) a front hollow needle portion (7) to be inserted into a body from which a sample is to be taken,
    a rear hollow needle portion (5) for communicating with the evacuated container (3),
    a conduit (11) connecting the front needle portion (7) to the rear needle portion (5), and
    (d) a valve mechanism (6) to open and close the conduit (11), the valve mechanism (6) being manually operable by one hand and controlling the application of negative pressure in the front needle portion (7), the valve mechanism (6) being moveable between a rest position in which the conduit (11) is closed and an activated position in which the conduit is open,
    the method comprising the steps of:
    (i) establishing communication between a pre-evacuated container (3) and the rear hollow needle portion (5);
    (ii) inserting the front needle portion (7) into the body from which the sample is to be taken at the appropriate location for obtaining the desired sample; the valve mechanism being in the rest position and the conduit being closed during steps (i) and (ii); and
    (iii) actuating the valve mechanism (6) for sufficient time, and repeatedly if desired, to open the conduit and to apply negative pressure in the front needle portion (7) so as to draw a sample through the front needle portion (7) through the conduit (11) to the rear needle portion (5) and into the pre-evacuated container (3).

* * * * *